US006785432B2

(12) United States Patent
Letant et al.

(10) Patent No.: US 6,785,432 B2
(45) Date of Patent: Aug. 31, 2004

(54) TARGET MOLECULES DETECTION BY WAVEGUIDING IN A PHOTONIC SILICON MEMBRANE

(75) Inventors: Sonia Letant, Benicia, CA (US); Anthony Van Buuren, Livermore, CA (US); Louis Terminello, Pleasanton, CA (US)

(73) Assignee: The Regents of the University of California, Oakland, CA (US)

( * ) Notice: Subject to any disclaimer, the term of this patent is extended or adjusted under 35 U.S.C. 154(b) by 118 days.

(21) Appl. No.: 10/159,175

(22) Filed: May 31, 2002

(65) Prior Publication Data

US 2002/0191884 A1 Dec. 19, 2002

Related U.S. Application Data

(60) Provisional application No. 60/298,442, filed on Jun. 15, 2001.

(51) Int. Cl.[7] .......................... G02B 6/00; G02B 6/10; G01N 21/01; G01N 21/29; G01J 1/04
(52) U.S. Cl. .......................... 385/12; 385/14; 385/129; 385/130; 250/227.11; 250/227.14; 422/82.05; 422/82.11
(58) Field of Search ................... 385/12, 14, 129–132; 250/227.11, 227.14; 422/82.05–82.11

(56) References Cited

U.S. PATENT DOCUMENTS

| 5,485,277 | A | * | 1/1996 | Foster ........................ 356/445 |
| 5,496,701 | A | * | 3/1996 | Pollard-Knight ............ 435/7.4 |
| 5,832,165 | A | * | 11/1998 | Reichert et al. ............ 385/130 |
| 6,023,540 | A | * | 2/2000 | Walt et al. .................... 385/12 |
| 6,146,767 | A | | 11/2000 | Schwartz et al. ........... 428/457 |
| 6,356,676 | B1 | * | 3/2002 | Herron et al. ................ 385/12 |
| 6,611,634 | B2 | * | 8/2003 | Herron et al. ................ 385/12 |
| 2003/0133639 | A1 | * | 7/2003 | Tao et al. ..................... 385/12 |

FOREIGN PATENT DOCUMENTS

| WO | WO01/36945 | 5/2001 | .......... G01N/21/45 |
| WO | WO01/36946 | 5/2001 | |

OTHER PUBLICATIONS

V. Lehmann; "The Physics of Macropore Formation in Low Doped n–Type Silicon" J. Electrochem. Soc., vol. 140 No. 10 Oct. 1993 pp. 2836–2843.
W. Vercoutere et al Rapid discrimination among individual DNA hairpin modecules at single–nucleotide resolution using an ion channel. Nature Biotechnology Mar. 2001 vol. 19 pp. 248–252.
Albert Birner et al "Silicon–Based Photonic Crystals" Adv. Materials 2001, 13, No. 6., Mar. 16 pp. 337–388.
K.B. Jirage "Nanotubule–based Molecular–Filtration Membranes" Science vol. 278 Oct. 1997 pp. 655–658.

\* cited by examiner

*Primary Examiner*—Brian Healy
*Assistant Examiner*—Kevin S. Wood
(74) *Attorney, Agent, or Firm*—Ann M. Lee; Alan H. Thompson; Eddie E. Scott

(57) ABSTRACT

Disclosed herein is a photonic silicon filter capable of binding and detecting biological and chemical target molecules in liquid or gas samples. A photonic waveguiding silicon filter with chemical and/or biological anchors covalently attached to the pore walls selectively bind target molecules. The system uses transmission curve engineering principles to allow measurements to be made in situ and in real time to detect the presence of various target molecules and determine the concentration of bound target.

10 Claims, 6 Drawing Sheets

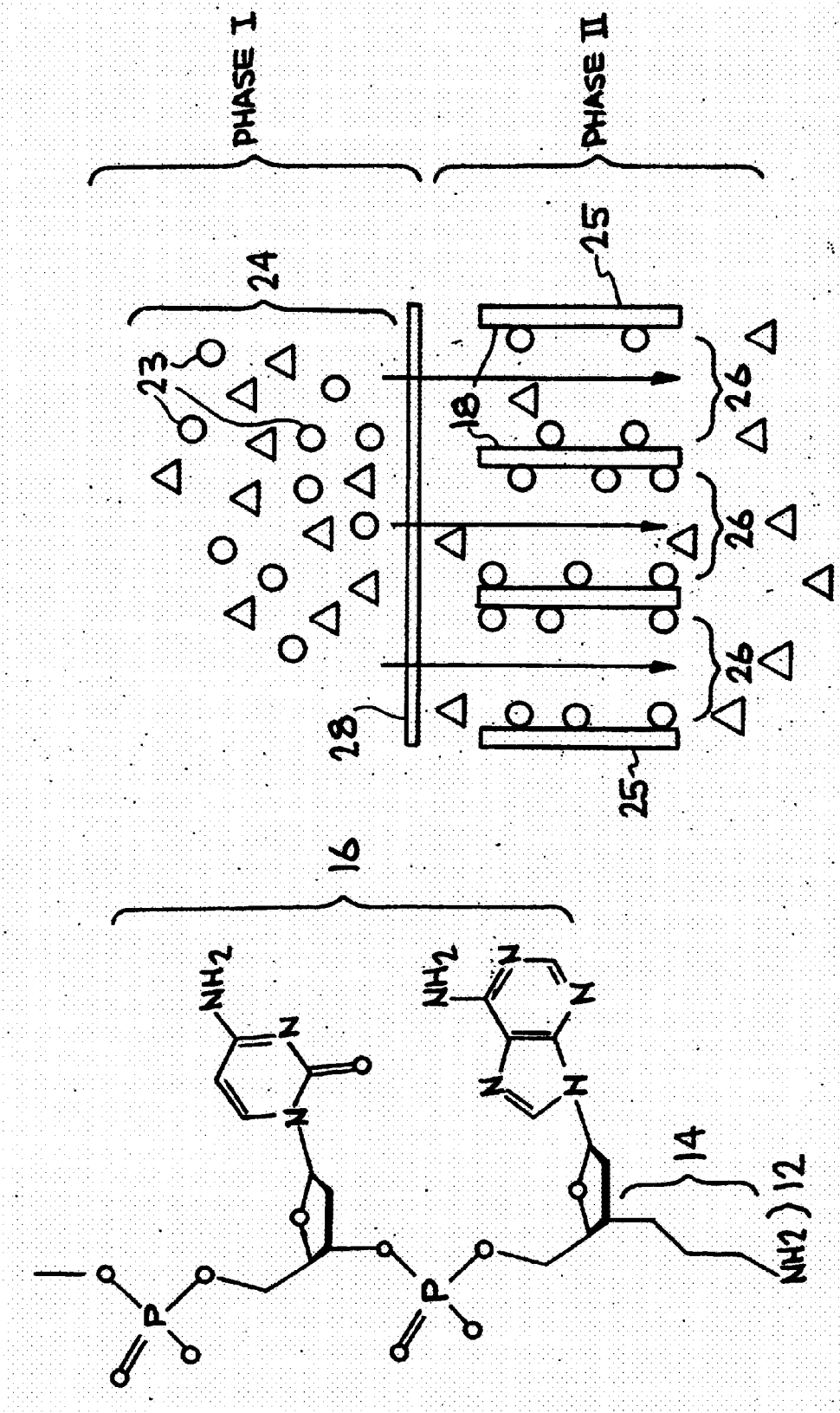

TARGET MOLECULES DETECTION BY WAVEGUIDING IN A PHOTONIC SILICON MEMBRANE

RELATED APPLICATION

This application claims priority in provisional application filed on Jun. 15, 2001, entitled "Detecting Chemical or Biological Target Molecules and Sequencing DNA by Waveguiding in a Silicon Membrane," serial No. 60/298,442, by inventor(s) Sonia E. Letant, Anthony W. Van Buuren and Louis J. Terminello.

The United States Government has rights in this invention pursuant to Contract No. W-7405-ENG-48 between the United States Department of Energy and the University of California for the operation of Lawrence Livermore National Laboratory.

BACKGROUND OF THE INVENTION

Extensive work has been performed during the last ten years to build and investigate photonic crystals, the optical analogues to electronic semiconductors. Photonic crystals are materials built to present a periodic variation of refractive index. The periodicity being the same order of magnitude as the wavelength of the electromagnetic (EM) waves, these structures exhibit band gaps for photons. The propagation of the EM waves can be controlled by changing the periodicity and introducing point or line defects in the photonic crystal. A. Birner et al in, "Silicon-based photonic crystals," *Adv. Mater.* 13, 377–388 (2001), recently reviewed 1D, 2D, and 3D photonic crystals made out of silicon.

Foresi et al in, "Photonic-bandgap microcavities in optical waveguides," *Nature* 390, 143–145 (1997), and Birner et al in, "Transmission of microcavity structure in a two-dimentional photonic crystal based on macroporous silicon," *Materials Science in Semiconductor Processing* 3, 487–491 (2000), disclose that 1D and 2D structures, respectively, are usually built by drilling well-controlled pores in a silicon wafer by electrochemical etch or by electron beam lithography. In, "Large-scale synthesis of a silicon photonic crystal with a complete three-dimensional bandgap near 1.4 micrometer," *Nature* 405, 437–440 (2000), Blanco et al disclose that 3D structures usually involve the growth of a crystal by chemical vacuum deposition on a periodic template followed by the dissolution of the template (inverse opal structure).

SUMMARY OF THE INVENTION

An aspect of the invention includes a photonic waveguiding device comprising: at least one silicon wafer having a plurality of through pores distributed according to a designed pattern leading to a photonic band gap; and at least one chemical or biological target specific anchor attached to the inner wall of at least one of the pores, wherein the anchor is capable of binding to a specific chemical or biological target molecule.

Another aspect of the invention includes a photonic waveguiding device comprising: an array of waveguiding filters, wherein each filter is functionalized with a chemical or biological target specific anchor to allow the contemporaneous detection of various chemical and biological target molecules and wherein each of the filters comprise (1) a silicon wafer having a plurality of through pores distributed according to a designed pattern leading to a photonic band gap and (2) a chemical or biological target specific anchor attached to the inner wall of at least one of the pores, the anchor being capable of binding to a chemical or biological target molecule.

A further aspect of the invention includes a photonic waveguiding detection system comprising: a light source; at least one silicon waveguiding filter, wherein the filter comprises a silicon wafer having (1) a plurality of through pores distributed according to a designed pattern leading to a photonic band gap and (2) at least one chemical or biological target specific anchor attached to the inner wall of at least one of the pores, wherein the anchor is capable of binding to a chemical or biological target molecule; a detector to count the photons transmitted through the device; and a computer to analyze the light transmitted through the filter by (1) recording the intensity and wavelength of light transmitted through the filter, (2) identifying the presence of target molecules bound in the device and (3) determining the concentration of bound target molecules.

A further aspect of the invention includes a method comprising:

measuring the transmission curve through at least one silicon filtering device, wherein the filtering device comprises (1) a plurality of through pores distributed according to a designed pattern leading to a photonic band gap and (2) at least one chemical or biological target specific anchor attached to the inner wall of at least one of the pores, wherein the anchor is capable of binding to a chemical or biological target molecule; passing a sample through the silicon filter, the sample being a gas or a liquid; shining a light orthogonal to the pores of the silicon filter, while contemporaneously flowing the sample through the filter; and measuring the transmission curve of the waveguiding silicon filter as the sample passes through the filter, wherein modifications in the transmission curve are (1) indicative that at least one of the target molecules has bound to the anchor and (2) indicative of the concentration of the bound target molecules.

Another aspect of the invention includes a method comprising:

fabricating a silicon membrane with an array of pores designed for opening a photonic band gap and for waveguiding; functionalizing the pore walls of the silicon membrane with chemical functional groups; and attaching biological or chemical anchors to the functionalized walls of the membrane to create a selective silicon photonic waveguiding filter.

BRIEF DESCRIPTION OF THE DRAWINGS

FIG. 3c shows the chemical structure of an amine functionalized single DNA strand.

FIG. 5 shows a silicon membrane used to separate two phases.

DETAILED DESCRIPTION

Theory

Figure 1A:
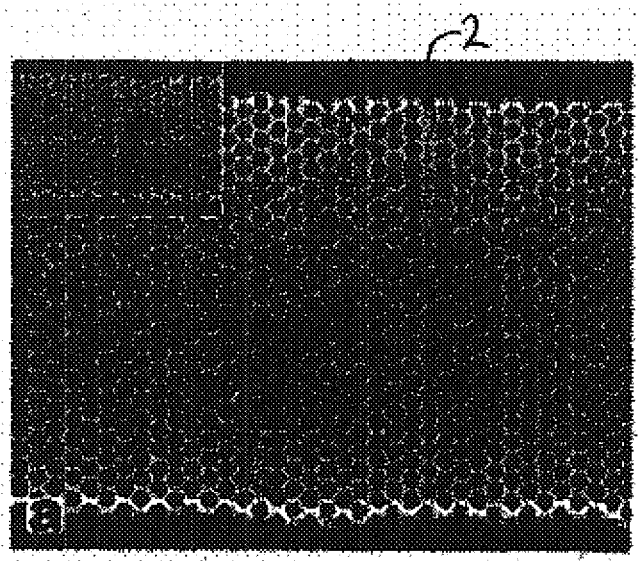
FIG. 1a is a top view SEM picture showing line defects embedded in 2D photonic silicon crystals.
Figure 1B:
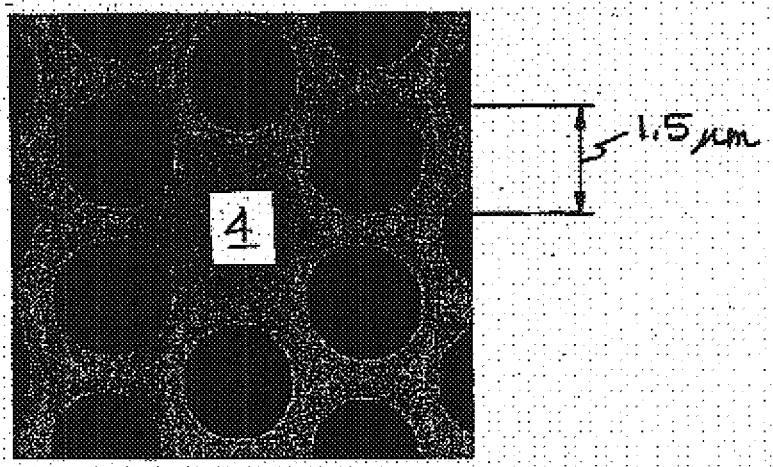
FIG. 1b is a top view SEM picture showing a point defect embedded in a 2D photonic silicon crystal.

Canham discloses in, "Quantum Wire Array Fabrication by Electrochemical and Chemical Dissolution," *Appl. Phys. Lett* 57,1046–1048 (1990), that randomly positioned pores can be created in silicon by electrochemical etch in an aqueous solution of hydrofluoric acid (HF), water and ethanol. Electrochemical parameters such as the current density, the HF concentration and the duration of the etch and physical parameters such as the doping type and level of the silicon substrate determine the diameter, length and density of the pores formed. Lehmann et al in, "Formation mechanism and properties of electrochemically etched trenches in n-type silicon," *J. Electrochem. Soc.* 137, 653–659 (1990), have shown that it is possible to pre-determine the location of the pores by patterning n-type silicon substrates with inverted pyramids (nucleation pits). These pits are made by standard lithography followed by potassium hydroxide (KOH) etch. The pores are then grown on the nucleation pits by applying back-side illumination during the HF electrochemical etch. The resulting material presents parallel pores, distributed according to the designed pattern. Any kind of pore pattern can potentially be achieved. Birner et al. in "Silicon-based photonic crystal,"*Adv. Mater.* 13, 377–388 (2001), disclose SEM top views of line and point defects embedded in 2D photonic silicon crystals, prepared by the electrochemical etching technique. The introduction of defects disturbs the translational symmetry of the periodic lattice and can lead to the formation of localized states (modes) in the band gap. FIGS. 1a and 1b are taken from the Birner et al disclosure. FIG. 1a demonstrates that line defects 2 and FIG. 1b demonstrates that point defects 4 can also be introduced in the pattern in order to engineer the transmission curve of the photonic crystal. Pore diameters can be tuned from about 1 micron to about 500 nanometers. A decrease of pore diameter to about 100 nm will allow the opening of photonic band gaps in the visible range.

Figure 2:
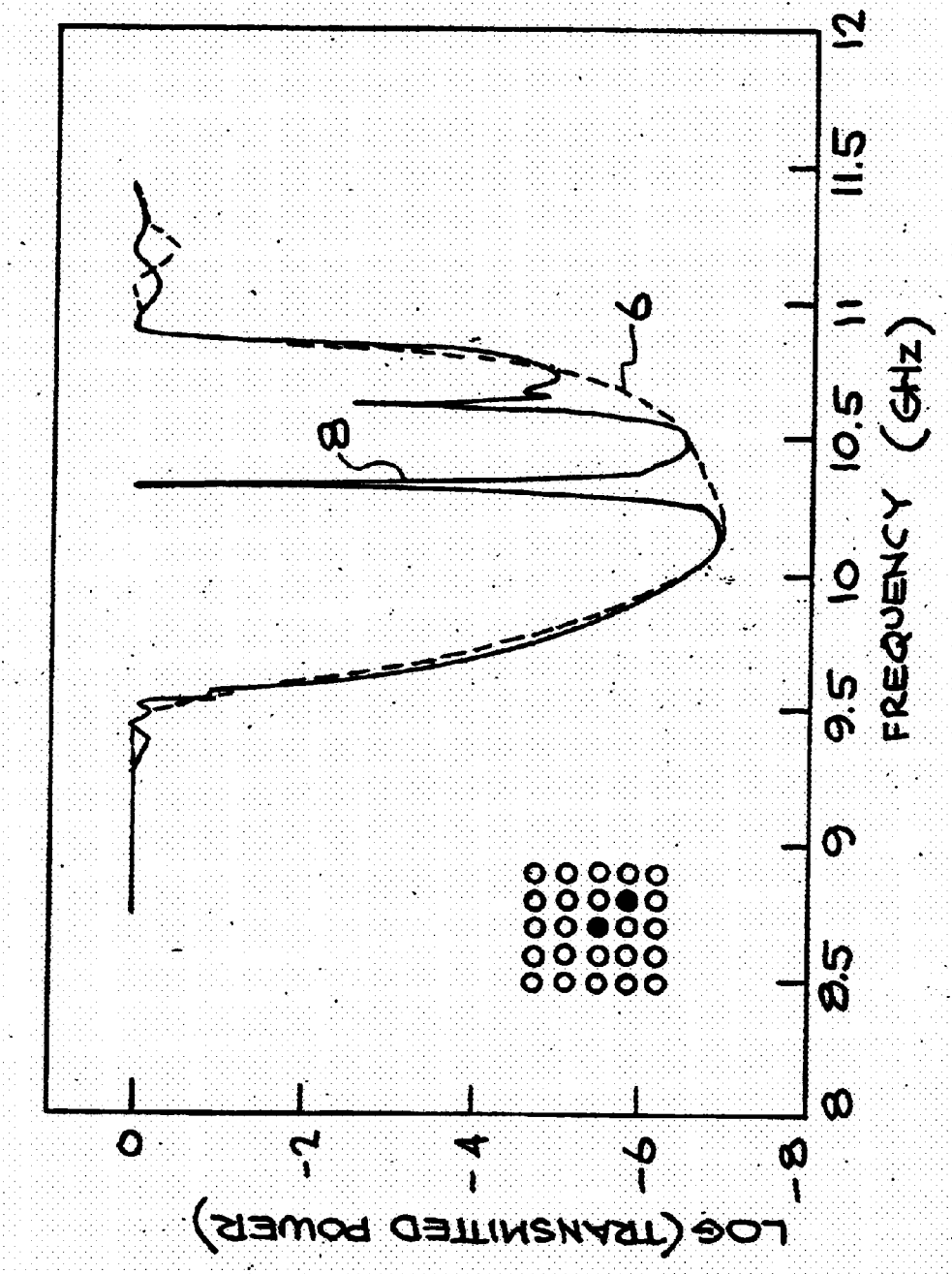
FIG. 2 is a graph of a calculated transmission curve for a perfect 2D photonic crystal and for the same crystal with two point defects.

In "Photonic band gaps and defects in two dimensions: studies of the transmission coefficient," *Phys. Rev. B* 48, 14121–14126 (1993), Sigalas et al. present the theory of propagation of EM waves in 2D photonic crystals made of dielectric rods separated by voids. This group investigated the case where EM waves propagate in a plane perpendicular to the axes of the cylinders for perfect crystals and for crystals with point defects. Experiments conducted by McCall et al. in "Microwave propagation in two-dimensional dielectric lattices," Phys. Rev. Lett. 67, 2017–2020 (1991), showed that the transmission curve of a perfect 2D photonic crystal presents band gaps and that the position of these band gaps depend on the periodicity, geometry and dielectric constant of the materials used. FIG. 2, taken from Sigalas et al, shows calculated transmission curves 6 and 8 (EM waves propagate in a plane perpendicular to the axes of the cylinders) for a perfect 2D photonic crystal 6 (dotted line) and for the same crystal with two point defects 8 (solid line). The two defects appear as two sharp modes in the phototonic band gap. FIG. 2 illustrates the effect of the introduction of point defects in a photonic crystal, which is to create localized states in the band gap.

The design of smart membranes through chemical functionalization of semi-conductor substrates with well-defined pore structures is described herein. A versatile class of new materials can be designed by attaching chemically or biologically specific anchors onto semi-conductor devices. Utilizing the well-defined pore morphology of silicon enhances the collection of targets and lowers the detection level. Novel membranes with the ability to selectively recognize and bind target molecules, such as proteins, DNA fragments, enzymes and other biologically and chemically relevant macromolecules, can be prepared by controlling both the pore morphology and the chemical affinity of the membrane surface.

Figure 3B:
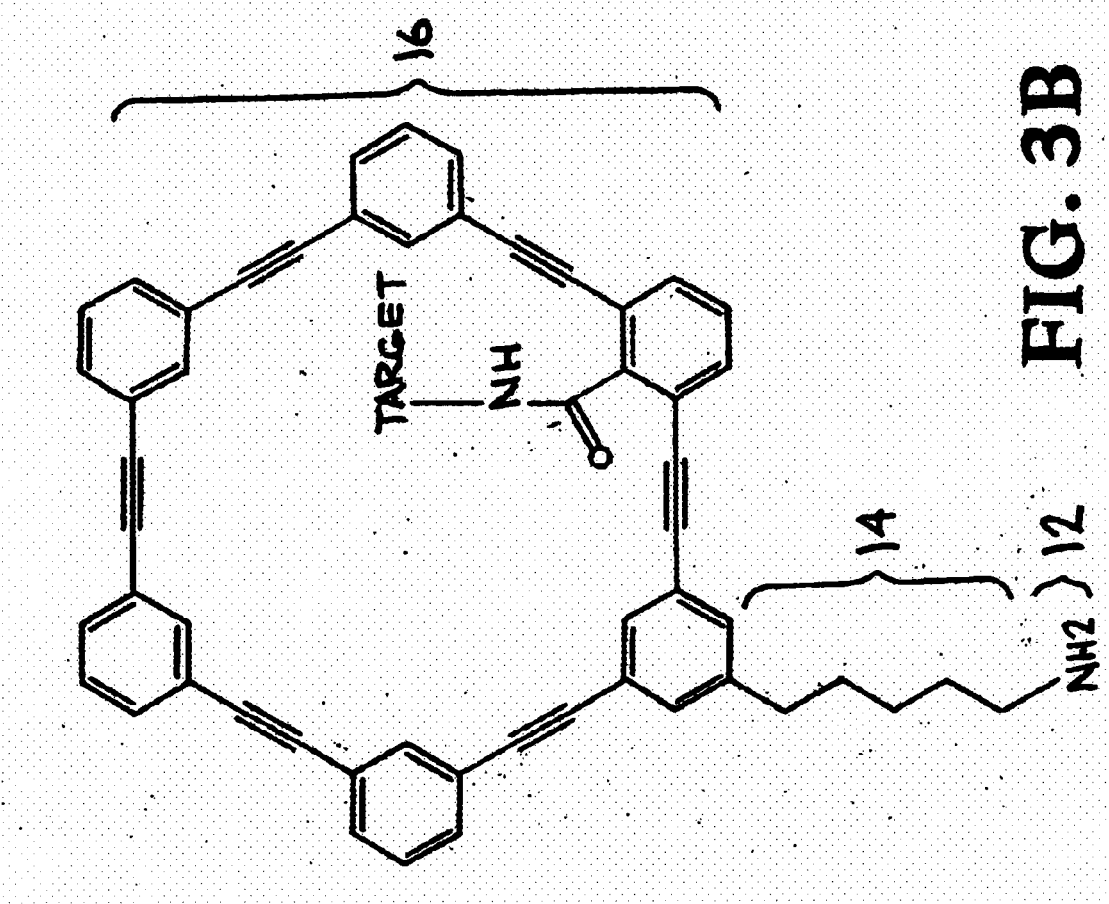
FIG. 3b shows the chemical structure of an amine functionalized macro-cycle.
Figure 3A:
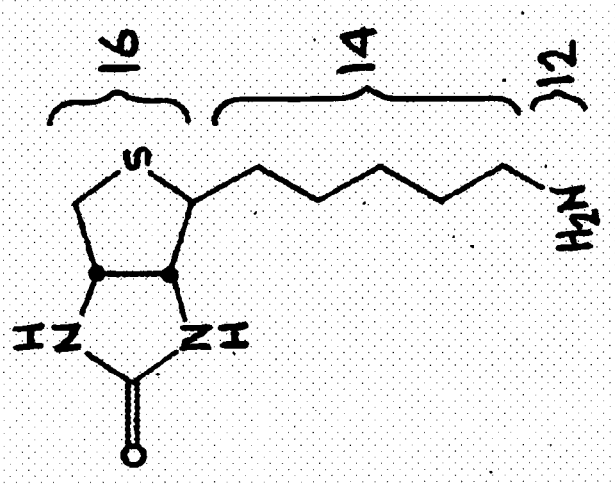
FIG. 3a shows the chemical structure of an amine functionalized biotin.
Figure 4:
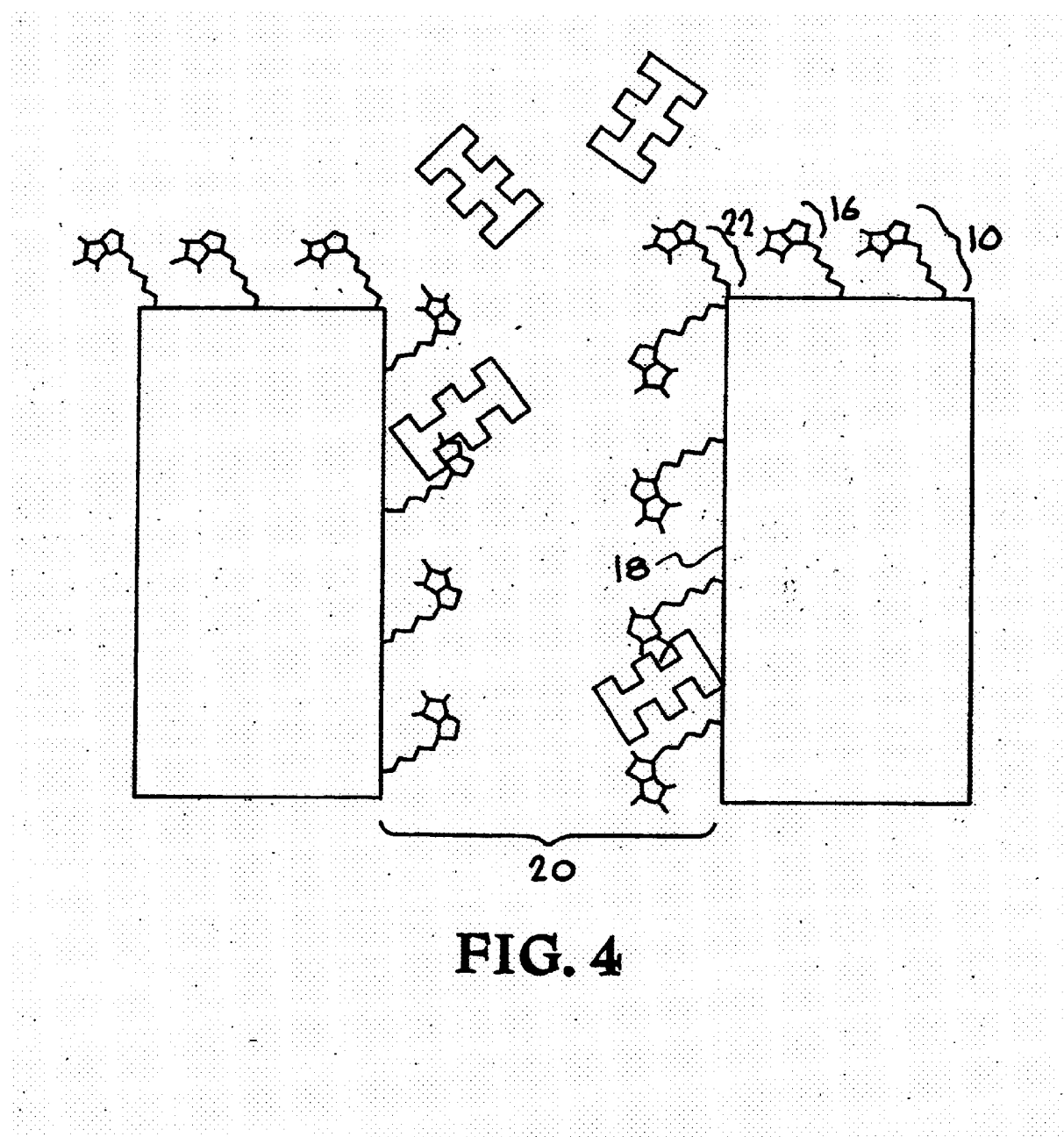
FIG. 4 is a schematic drawing of a pore functionalized with biotin exposed to streptavidin target molecules. (Not to scale)

Referring to FIGS. 3a, 3b, and 3c, membrane surfaces can be designed which selectively recognize and bind specific molecules. Chemical or biological anchors 10 typically comprise a functional group 12, a tether 14 (i.e., a carbon chain), and a receptor group 16 (e.g., an antibody, a single strand of DNA, a functionalized macro-cycle). Referring to FIG. 4, these anchors 10 are immobilized on the pore walls 18 via covalent attachment of the tether. Chemical or biological selectivity is given by the receptor group on the anchor. The diameter of the pores 20, the length of the tether 22, and the nature of the receptor group 16 can be controlled and tailored to suit a variety of applications.

Surface chemistry can be used to filter out and/or detect specific chemical or biological target molecules. In addition, the binding of the target molecules to the anchors is not permanent. The receptor groups on the anchor can be treated to remove the target molecules and the filter reused. For example, a sulfur-sulfur bridge (S—S) can be introduced in the alkyl chain of the tether. Once the target is bound to the anchor and the experiment is finished, the S—S bridge can be reduced by addition of dithiothreitol (DTT) and the surface of the filter can be regenerated by reacting it with a new receptor group.

Fabrication and Functionalization

100 $\mu$m thick Si wafers are commercially available. Extra thinning can be achieved by mechanical or chemical polishing or by microfabrication techniques if necessary. A thin (ranging between a few hundred nanometers and a few hundred microns) silicon wafer, which is by definition a waveguide when standing in a low refractive index medium like air or water, can be converted into a photonic waveguiding filter by electrochemically etching pores through the wafer. A silicon membrane with an array of pores designed for waveguiding can be prepared using the techniques described in "Formation mechanism and properties of electrochemically etched trenches in n-type silicon," *J. Electrochem. Soc.* 137, 653–659 (1990) by Lehmann et al. For example, a triangular or hexagonal array of holes can be etched through a thin slab of silicon, wherein the light is guided in the device by total internal reflection. In the alternative, a line defect (e.g., like the one shown in FIG. 1a) can be introduced in the array of holes, wherein the light is then guided by the photonic crystal. This type of silicon membrane can be used to separate two phases.

Referring to FIG. 5, specific target molecules 23 can be removed from the first phase. Transport between the two phases through the membrane 25 can occur under the action of a driving force such as a concentration or a pressure difference.

After electrochemical formation in HF, the silicon pore walls 18 are passivated by hydrogen (they are covered by Si—H bonds). These Si—H bonds can be functionalized in two distinct ways. The first method employs ozone oxidation of the pore walls, which results in the generation of a hydroxylated silicon oxide surface, i.e., silanol bonds (Si—OH). The ozone oxidation is followed by condensation of the silanol groups with functionalized silanes, as described in Janshoff et al., "Macroporous p-type silicon Fabry-Perot layers. Fabrication, characterization, and applications in biosensing," *J. Am. Chem. Soc.* 120, 12108–12116 (1998). The second method employs hydrosilylation of alkenes or alkynes as described in Buriak et al., "Lewis acid mediated hydrosilylation on porous silicon," *J. Am. Chem. Soc.* 121, 11491–11502 (1999), followed by a reduction and subsequent reaction with functionalized groups such as esters. The properties of the resulting functionalized silicon pore surface, such as coverage, uniformity and stability, can then be characterized by a variety of techniques. Surface characterization measurements using atomic force microscopy (AFM), photoelectron spectroscopy (PES), soft X-ray fluorescence (SXF), X-ray absorption spectroscopy (XAS), Fourier Transform Infra Red Spectrometry (FTIR) and Mass Spectrometry (MALDI, MS) can be used to characterize the surface properties.

Under the first functionalization method, ozone oxidation of the pores generates a hydroxylated silicon oxide surface (silanol, Si—OH) which allows for subsequent condensation of the Si—OH groups along the pore walls with functionalized silanes. Some examples of functionalized silanes include $R'R_2Si(OCH_3)$ where $R=CH_3$ and $R'=$ a functional moiety such as, amine, thiol or modified ester. These functional groups can be reacted with cross linkers and then with biological or chemical anchors like antibodies and cyclodextrins. Cross linkers are carbon chains with functional groups designed to bind two molecules together, or to bind a molecule to a surface. Dancil et al. have designed porous Si biosensors that can detect antibody-antigen binding with this technique (see Dancil et al, "A Porous Silicon Optical Biosensor: Detection of Reversible Binding of IgG to a Protein A-Modified Surface," *J. Am. Chem. Soc.* 121, 11491–11502, 1999).

Under the second functionalization method, no oxidation is required. The hydride terminated silicon pore walls (Si—H) are reacted with alkenes or alkynes. This reaction leads to nitrile (—CN) terminated alkyl chains covalently attached on silicon via silicon-carbon bonds (Si—C). This reaction can be catalyzed by an aluminum based Lewis acid or thermally. The nitrile groups are then reduced to amine groups ($NH_2$) and the biological or chemical anchors are attached as described above in the first functionalization method.

Fabrication of Porous Silicon

Silicon Substrate

Step 1: Pre-patterning

Nucleation sites (inverted pyramids) are prepared on the surface of an n-type (phosphorus doped) silicon wafer by microfabrication (silicon nitride mask, photolithography and KOH etch). The silicon wafer is oriented orthogonal to the <100> crystallographic direction and the pores will grow along the <100> direction (orthogonal to the silicon wafer surface). The design of the mask corresponds to the geometry of the array: each inverted pyramid will correspond to a pore. There is no limitation on the design.

Step 2: Pore etching

The patterned substrate is mounted in a PVC electrochemical cell. The electrolyte is a mixture of hydrofluoric acid (HF), water and ethanol. The typical composition of the electrolyte solution is: 5% HF, 80% water and 15% ethanol by volume. Ethanol can also be replaced by a few drops of surfactant like Mirasol™ or Ilfotol™. The counter electrode is made out of platinum and is submerged in the electrolyte. The working electrode is contacted to the back of the substrate via indium gallium eutectic paste. The dissolution of silicon by HF requires the presence of positive charges. Since these charges cannot come from the doping in n-type silicon substrates, they are generated by back-side illumination. A tungsten halogen lamp is focused on the back of the sample and the infra-red (IR) wavelengths are removed with an IR filter. An ammeter measures the current photo-generated in the silicon wafer (photocurrent) and a constant voltage is applied between the two electrodes to induce an electric field attracting the positive charges on the nucleation sites (tip of the inverted pyramids). The pore length is proportional to the duration of the etch. The pore diameter increases with the photocurrent (the light intensity). Typical conditions to etch 500 nm diameter pores are: [HF]=5% by volume, 3 V applied and a photocurrent of 3 $mA/cm^2$.

Surface Activation

Ozone Oxidation

Freshly etched silicon samples are exposed to ozone using an ozone generator for a few minutes. This provides an oxidized silanol (Si—OH) terminated surface. The samples are then refluxed overnight at room temperature in a 50 mM solution of functionalized methoxysilane in toluene. After this first step, the samples are rinsed with toluene, ethanol, water and acetone and then dried under a stream of nitrogen. This procedure has been published by Janshoff et al. in "Marcroporous p-type silicon Fabry-Perot layers. Fabrication, characterization, and applications in biosensing," *J. Am. Chem. Soc.* 120, 12108–12116 (1998).

(2) Hydrosilylation

Freshly etched silicon samples are placed in a round-bottom flask. The flask is evacuated, filled with nitrogen and sealed with a septum. A 1.0 M hexane solution of $EtAlCl_2$ is dropped onto the sample surface with a microliter syringe through the rubber septum, followed by an addition of the alkene (ex: pentene, dodecene) or alkyne (ex: pentyne, dodecyne), also via the septum. The sample is then left to react for 1–2H for the alkynes and for at least 12H for the alkenes. The sample is then quenched under inert atmosphere with THF, followed by $CH_2Cl_2$ and then removed to the ambient atmosphere. Finally, it is rinsed with ethanol and dried under a stream of nitrogen. This procedure has been published by Buriak et al. in "Lewis acid mediated hydrosilylation on porous silicon", *J. Am. Chem. Soc.* 121, 11491–11502 (1999). The same procedure can be done by thermal instead of chemical catalysis. In this case no $EtAlCl_2$ is added. Instead, the sample is covered with undecylenic acid and allowed to react at 95° C. for 16H. This procedure has been published by Boukherroub et al. in "Thermal hydrosilylation of undecylenic acid with porous silicon", *E.C.S.* 149, H59–63 (2002).

At the end of the surface activation (for both ozone oxidation and hydrosilylation) functional groups are attached to the silicon surface via a carbon chain (tether) covalently linked to the pore wall by a silicon-oxygen-silicon bond (Si—O—Si—R) or by a silicon-carbon bond (Si—C—R). Examples of functional groups are: amine (—$NH_2$), thiol (—SH) and esters like the standard maleimidobutyryloxydosuccinimide ester.

Functionalization of Porous Silicon

Once the functional groups described above are attached to the silicon pore walls, the immobilization of the chemical or biological anchors is done by standard cross linking chemistry. Examples of target molecule-anchor pairs include: any antigen-antibody pair, any single DNA-single DNA compliment pair, and any molecule, cell, bacteria or virus for which a specific anchor can be designed. Specific examples of anchors include the antibody biotin and the macro-cycle cyclodextrins. Many of these anchor molecules are commercially available with amine groups (—$NH_2$)

ready to react with silicon surfaces that are activated with a modified ester such as, maleimidobutyryloxydosuccinimide ester.

Some specific examples of anchor-target molecule pairs follow: (1) the apolar lumen of cyclodextrins trap hydrophobic target molecules, (2) carbohydrates specifically bind to cell membrane proteins like lectins, (3) TWTCP (tetratryptophan ter-cyclo pentane) specifically binds to diphosphoril lipid which is present in the outer cellular membrane of gram-(-) bacteria, and (4) virus attachment on cells comprises the binding of a viral attachment protein to a cellular receptor, e.g., the haemagglutinin of Infuenza virus specifically binds to sialyoglycosaccharides and the glycoproteins of HIV bind to CD-4 proteins.

Immobilization of an amine functionalized anchor on a silicon surface activated with a modified ester can be done by incubating the silicon sample in a solution of the anchor molecule (1 mg/ml) in phosphate buffered saline (PBS) and DMSO for 30 min at room temperature. The sample is rinsed with DMSO, water and PBS. Similar procedures can be applied to the immobilization if the silicon surface is activated with an amine group. In that case, a modified ester functionalized anchor can be used.

Filter and Detection System

Figure 6:
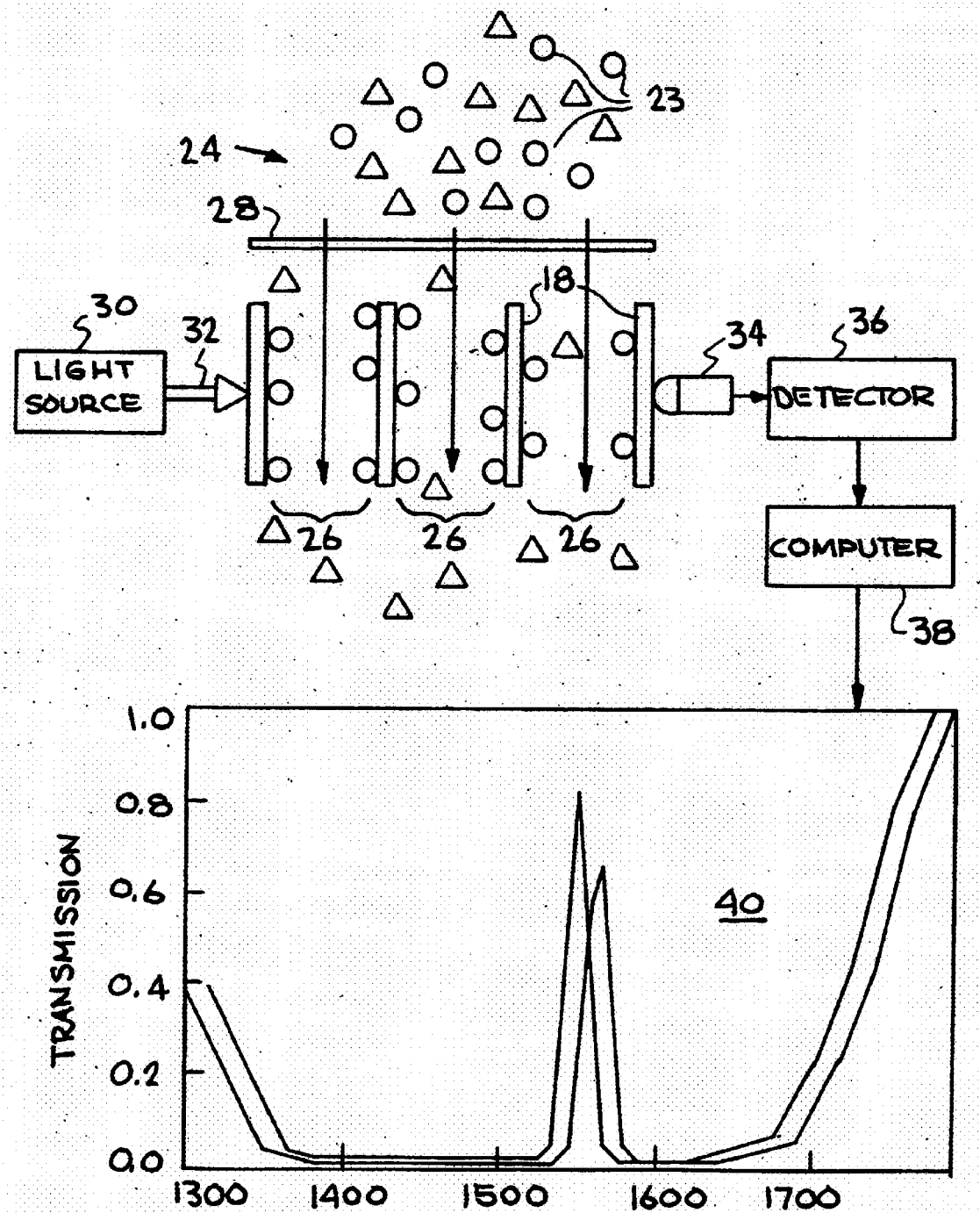
FIG. 6 is a schematic drawing of a photonic waveguiding filter system.

FIG. 6 shows a schematic of a photonic waveguiding filter system in which a gas or liquid sample 24 to be analyzed runs parallel through a plurality of pores 26 having receptor-containing pore walls 18 in a photonic waveguiding silicon filter 28 while the transmission curve, i.e., the intensity of light transmitted through the device versus wavelength, is measured in real time. This system employs the end-fire coupling technique. Basically, light from a light source 30 is coupled into the device via a fiber optic 32 and a lens (not shown). An optical microscope (not shown) may be used to position the fiber optic on the waveguide. Light is then transmitted orthogonally to the pores through the photonic waveguiding silicon filter, detected by a microscope objective 34 and focused on a detector 36. Photomultiplier tubes or photodiodes are examples of effective detectors. A computer 38 converts the data to produce a graph 40 of the transmission curve, i.e., the intensity of the light transmitted through the photonic filter versus the wavelength. It detects the presence of a target 23 bound in the device and calculates its concentration.

The silicon waveguiding collection and detection filter allows measurements in situ and in real time. The filter can be used to monitor air pollution, water contamination, and to detect the presence of specific chemical or biological molecules in gas or liquid samples. The filter can be made to have dimensions less than 200 $\mu$m×1 cm×1 cm. The full device, with the optics, can be engineered to fit in one hand and a laptop computer can be attached to the system to read the target concentration data.

Binding of target molecules on the receptor-containing pore walls is detected by a shift of the transmission curve of the waveguiding filter due to an increase of the dielectric constant of the pores. In this configuration, as the gas or liquid to be analyzed runs through the pores, target molecules will bind to the anchors that have been attached to the pore walls. The device will operate with or without the introduction of defects in the waveguide. However, the introduction of defects in the waveguide can dramatically increase the sensitivity of the device because a small shift of position of a sharp spectral feature induces a large intensity difference at a given wavelength. Referring to FIG. 6, graph 40 illustrates that, if following a sharp mode in the band gap (defect), a small spectral shift can induce a large intensity shift at a given wavelength.

The sensitivity of the device is maximized by calculating the optimal pore size and pore spacing along with the position of the defects, i.e., missing pores. The transfer-matrix technique for the propagation of EM waves in dielectric structures described by Sigalas et al in, "Photonic band gaps and defects in two dimensions; studies of the transmission coefficient", *Phys. Rev.* B48, 14121–14126 (1993), can be adapted to perform the calculations. The system studied by Sigalas et al. uses silicon rods in air and the present system uses air rods in silicon, so a change of the dielectric constants entered in the program is required. The transfer-matrix technique takes into account dispersion, i.e., the variation of the dielectric constant with the wavelength, and absorption. It also allows the introduction of multiple defects in the periodic structure of the photonic crystal.

The transmission curves of the photonic filters are calculated when the device is in air (for gas phase applications) or buffer (for liquid phase applications) and has no target molecules bound to it. The same calculations are then performed after target molecules bind. The spectral shift of the band edge and/or of the defect states in the band gap due to the binding of the target molecules can be extracted for various device configurations (pore size, pore spacing, defect nature and position). The optimal configuration can be deduced theoretically and then built and tested. Pores having diameters ranging in size from about 50 nanometers to about 1 micron are effective and can be fabricated by the process outlined above. The pore diameter should be adapted to the target. For example, detection of large biological targets such as bacteria require pores in the micron range. Viruses and large proteins require pores in the 100 nm range. Small proteins and chemical compounds require pores in the 50 nm range. The higher the change of refractive index of the pore upon binding, the higher the shift in the transmission curve and the lower the detection level. The refractive index change scales with the filling fraction of the pore by the target. Therefore, a pore size adjusted to the target size will increase the filling fraction for low concentrations and the refractive index change will be optimized. It is also important to note that a modification of pore diameter induces a spectral shift of the band gap. The wavelength of light shone through the device will then have to be adjusted to probe the relevant spectral region. For example, micron sized pores lead to band gaps in the IR range and 100 nm sized pores lead to band gaps in the visible range.

While various materials, parameters, operational sequences, etc. have been described to exemplify and teach the principles of this invention, such are not intended to be limited. Modifications and changes may become apparent to those skilled in the art; and it is intended that the invention be limited only by the scope of the appended claims.

The invention claimed is:

1. A photonic waveguiding device comprising:
    at least one silicon wafer having a plurality of through pores distributed according to a designed pattern leading to a photonic band gap; and
    at least one chemical or biological target specific anchor attached to the inner wall of at least one of said pores, wherein said anchor is capable of binding to a specific chemical or biological target molecule.
2. The photonic waveguiding device recited in claim 1, wherein said pores have pore diameters ranging in size from about 50 nm to about 1 $\mu$m.
3. The photonic waveguiding device recited in claim 1, wherein said anchor is attached to said pore wall via silicon-carbon or silicon-oxygen-carbon covalent bonding.
4. The photonic waveguiding device recited in claim 1, wherein the total size of said device has dimensions no larger than 200 $\mu$m×1 cm×1 cm.

5. A photonic waveguiding device comprising:

an array of waveguiding filters, wherein each filter is functionalized with a chemical or biological target specific anchor to allow the contemporaneous detection of various chemical and biological target molecules and wherein each of said filters comprise (1) a silicon wafer having a plurality of through pores distributed according to a designed pattern leading to a photonic band gap and (2) a chemical or biological target specific anchor attached to the inner wall of at least one of said pores, said anchor being capable of binding to a chemical or biological target molecule.

6. A photonic waveguiding detection system comprising:

a light source;

at least one silicon waveguiding filter, wherein said filter comprises a silicon wafer having (1) a plurality of through pores distributed according to a designed pattern leading to a photonic band gap and (2) at least one chemical or biological target specific anchor attached to the inner wall of at least one of said pores, wherein said anchor is capable of binding to a chemical or biological target molecule;

a detector to count the photons transmitted through the device; and a computer to analyze the light transmitted through the filter by (1) recording the intensity and wavelength of light transmitted through the filter, (2) identifying the presence of target molecules bound in the device and (3) determining the concentration of bound target molecules.

7. A method comprising:

measuring the transmission curve through at least one silicon filtering device, wherein said filtering device comprises (1) a plurality of through pores distributed according to a designed pattern leading to a photonic band gap and (2) at least one chemical or biological target specific anchor attached to the inner wall of at least one of said pores, wherein said anchor is capable of binding to a chemical or biological target molecule;

passing a sample through said silicon filter, said sample being a gas or a liquid;

shining a light orthogonal to the pores of said silicon filter, while contemporaneously flowing said sample through said filter; and measuring the transmission curve of said waveguiding silicon filter as said sample passes through said filter, wherein modifications in said transmission curve are (1) indicative that at least one of said target molecules has bound to said anchor and (2) indicative of the concentration of said bound target molecules.

8. The method of claim 7, further comprising:

releasing the bound target molecules from the pore walls after measuring the transmission curve, wherein said transmission curve was generated by passing said sample through said filtering device.

9. The method of claim 8, further comprising:

regenerating said filtering device after releasing the bound target molecules from the pore walls by adding a plurality of chemical or biological target specific anchor molecules to the pores of said filtering device, said anchor molecules being capable of binding to specific chemical or biological target molecules.

10. A method comprising:

fabricating a silicon membrane with an array of pores designed for opening a photonic band gap and for waveguiding;

functionalizing the pore walls of the silicon membrane with chemical functional groups; and attaching biological or chemical anchors to the functionalized pore walls of said membrane to create a selective silicon photonic waveguiding filter, wherein the anchors contain chemically or biologically active receptor groups at the end not attached to the pore walls.

* * * * *